US011344531B2

(12) United States Patent
Acuña Castroviejo et al.

(10) Patent No.: US 11,344,531 B2
(45) Date of Patent: May 31, 2022

(54) DURABLE PREPARATION OF AN INJECTABLE OF MELATONIN EXHIBITING LONG-TERM STABILITY

(71) Applicants: SERVICIO ANDALUZ DE SALUD, Seville (ES); UNIVERSIDAD DE GRANADA, Granada (ES)

(72) Inventors: Darío Acuña Castroviejo, Granada (ES); Germaine Escames Rosa, Granada (ES); Pablo Bueno Laraño, Granada (ES); Alfonso Mansilla Roselló, Granada (ES); José Antonio Ferrón Orihuela, Granada (ES); José Jorge Hernández Magdalena, Granada (ES); Miguel Ángel Calleja Hernández, Granada (ES); Desirée González Callejas, Granada (ES); Ana Comino Pardo, Granada (ES); Carmen Olmedo Martín, Granada (ES); Carmen Venegas Maldonado, Granada (ES)

(73) Assignees: Servicio Andaluz de Salud, Seville (ES); Universidad de Granada, Granada (ES)

( * ) Notice: Subject to any disclaimer, the term of this patent is extended or adjusted under 35 U.S.C. 154(b) by 0 days.

(21) Appl. No.: 15/129,327

(22) PCT Filed: Mar. 27, 2015

(86) PCT No.: PCT/ES2015/070236
§ 371 (c)(1),
(2) Date: Sep. 26, 2016

(87) PCT Pub. No.: WO2015/144965
PCT Pub. Date: Oct. 1, 2015

(65) Prior Publication Data
US 2017/0112810 A1    Apr. 27, 2017

(30) Foreign Application Priority Data
Mar. 27, 2014    (ES) .................. ES201430442

(51) Int. Cl.
*A61K 31/4045*    (2006.01)
*A61K 47/10*    (2017.01)
*A61K 9/00*    (2006.01)
*A61K 9/19*    (2006.01)
*A61K 45/06*    (2006.01)

(52) U.S. Cl.
CPC ........ *A61K 31/4045* (2013.01); *A61K 9/0019* (2013.01); *A61K 9/19* (2013.01); *A61K 45/06* (2013.01); *A61K 47/10* (2013.01)

(58) Field of Classification Search
CPC .. A61K 31/4045; A61K 45/06; A61K 9/0019; A61K 9/19; A61K 47/10
See application file for complete search history.

(56) References Cited

U.S. PATENT DOCUMENTS

| 4,855,305 A * | 8/1989 | Cohen .................... A61P 15/18 514/171 |
| 5,939,084 A * | 8/1999 | Simon .................... A61K 8/492 424/401 |
| 2005/0164987 A1* | 7/2005 | Barberich .......... A61K 31/4045 514/58 |
| 2010/0286121 A1* | 11/2010 | Rohrs .................. A61K 9/0019 514/211.15 |

FOREIGN PATENT DOCUMENTS

| CN | 101966167 A | 2/2011 | |
| WO | 2005/062992 A2 | 7/2005 | |
| WO | 2010062153 A1 † | 6/2010 | |
| WO | WO2010/062153 * | 6/2010 | ......... A61K 31/4045 |
| WO | WO-2010062153 A1 | 6/2010 | |
| WO | WO-2012156565 A1 | 11/2012 | |
| WO | 2013068565 A1 † | 5/2013 | |
| WO | WO-2013068565 A2 | 5/2013 | |

OTHER PUBLICATIONS

Jeff Johns et al (JAASP 2012;1(1):32-43) (Year: 2012).*
Garcia et al (WO2010/062153) translation (Year: 2010).*
Acuña Castroviejo et al., Melatonin-mitochondria interplay in health and disease. Curr Top Med Chem. 2011;11(2):221-40.
Acuña-Castroviejo et al., Extrapineal melatonin: sources, regulation, and potential functions. Cell Mol Life Sci. Aug. 2014;71(16):2997-3025.
Carrillo-Vico et al., Beneficial pleiotropic actions of melatonin in an experimental model of septic shock in mice: regulation of pro-/anti-inflammatory cytokine network, protection against oxidative damage and anti-apoptotic effects. J Pineal Res. Nov. 2005;39(4):400-8.
Chahbouni et al., Melatonin treatment normalizes plasma pro-inflammatory cytokines and nitrosative/oxidative stress in patients suffering from Duchenne muscular dystrophy. J Pineal Res. Apr. 2010;48(3):282-9.
Gitto et al., Melatonin reduces oxidative stress in surgical neonates. J Pediatr Surg. Feb. 2004;39(2):184-9.
Kücükakin et al., Oxidative stress in relation to surgery: is there a role for the antioxidant melatonin? J Surg Res. Apr. 2009;152(2):338-47.
Kücükakin et al., Utility of melatonin to treat surgical stress after major vascular surgery—a safety study. J Pineal Res. May 2008;44(4):426-31.

(Continued)

*Primary Examiner* — Sahar Javanmard
(74) *Attorney, Agent, or Firm* — McCarter & English, LLP; Jill Mello

(57) ABSTRACT

The invention relates to an aqueous melatonin composition exhibiting surprising long-term stability and allowing high concentrations of said water-insoluble active ingredient. The properties of said composition render it useful as an injectable, for example, for the intravenous administration thereof.

11 Claims, No Drawings

(56) References Cited

OTHER PUBLICATIONS

Mohan et al., Melatonin in critically ill patients. Acta Anaesthesiol Scand. Oct. 2005;49(9):1397.
Molina-Carballo et al., Utility of high doses of melatonin as adjunctive anticonvulsant therapy in a child with severe myoclonic epilepsy: two years' experience. J Pineal Res. Sep. 1997;23(2):97-105.
Mundigler et al., Impaired circadian rhythm of melatonin secretion in sedated critically ill patients with severe sepsis. Crit Care Med. Mar. 2002;30(3):536-40.
Naguib et al., Pharmacological effects of intravenous melatonin: comparative studies with thiopental and propofol. Br J Anaesth. Apr. 2003;90(4):504-7.
Reiter et al., A review of the evidence supporting melatonin's role as an antioxidant. J Pineal Res. Jan. 1995;18(1):1-11.
Sánchez-Barceló et al., Clinical uses of melatonin: evaluation of human trials. Curr Med Chem. 2010;17(19):2070-95.
International Search Report in International Application No. PCT/ES2015/070236, dated May 20, 2015 (4 pages).
Lopez, et al., "Identification of an inducible nitric oxide synthase in diaphragm mitochondria from septic mice Its relation with mitochondrial dysfunction and prevention by melatonin", *The International Journal of Biochemistry & Cell Biology* (2006), vol. 38, pp. 267-278.
Xiang et al., Treatment Progress of Melatonin for Critical Illness. Occup. and Health. Aug. 16, 2011; 27(16):1897-1900.
Cheung, et al, Preclinical evaluation of pharmokinetics and safety of melatonin in propylene glycol for intravenous administration, J Pineal Res Nov. 2006 41(4) 337-43.†

\* cited by examiner
† cited by third party

DURABLE PREPARATION OF AN INJECTABLE OF MELATONIN EXHIBITING LONG-TERM STABILITY

RELATED APPLICATIONS

This application is a 35 U.S.C. § 371 national stage filing of International Application No. PCT/ES2015/070236, filed on Mar. 27, 2015, which claims priority to Spanish Patent Application No. P201430442, filed on Mar. 27, 2014. The entire contents of each of the foregoing applications are incorporated herein by reference.

FIELD OF THE INVENTION

The present invention is comprised in the field of medicine and pharmacy and relates to an injectable composition of melatonin having high stability. The present invention also relates to the use of said composition as a medicinal product and to its use in the treatment of various conditions, such as sepsis for example.

STATE OF THE ART

Melatonin (N-acetyl-5-methoxy-tryptamine) is an endogenous neurohormone physiologically produced by the pineal gland (epiphysis cerebri). Its rate of secretion follows a circadian rhythm linked to the light-dark cycle, and it plays a fundamental role in inducing sleep. Furthermore, it has been found that melatonin plays a fundamental role in inflammatory response regulation, since it acts as a potent scavenger of oxygen free radicals that are generated, for example, during sepsis and the subsequent development of systemic inflammatory response syndrome (SIRS) and the subsequent multiple organ dysfunction syndrome (MODS), which is also known as multiple organ failure; during myocardial infarctions; in mitochondrial damage; in abdominal surgery processes; in pulmonary edema; and in kidney or liver failure.

It is known to activate antioxidant enzyme pathways (superoxide dismutase, glutathione peroxidase, glutathione reductase) (Reiter et al. 1995. J Pineal Res 18:1-11), to regulate mitochondrial homeostasis (Acuña-Castroviejo et al. 2011. Curr Top Med Chem 11:221-240), to reduce the total number of circulating polymorphonuclear leukocytes and serum malondialdehyde levels (Gitto et al., 2004. J Pediatr Surg 39: 184), to modulate monocytes, NK and the production of cytokines, and to inhibit apoptosis (Mundigler et al., 2002. Crit Care Med 30:536-40; Carrillo-Vico et al. 2005. J Pineal Res 39:400-408), and to reduce proinflammatory cytokine levels and oxidative damage in patients with Duchenne muscular dystrophy (Chahbouni et al. 2010, J Pineal Res 48:282-289), among other functions. It has also been found that in critical patients with sepsis there is a disruption in the circadian rhythm of melatonin, while endogenous secretion of melatonin is preserved in patients without sepsis (Mundigler et al., 2002. Crit Care Med 30:536-40).

Its therapeutic usefulness has been demonstrated in different pathologies (Sánchez-Barceló et al. 2010, Curr Med Chem 17:2070-2095), where as a general rule it shows a lack of toxicity after administration (Acuña-Castroviejo et al. 2014. Cell Mol Life Sci DOI: 10.1007/s00018-014-1579-2). It has therefore been used successfully in the treatment of epilepsy (Molina-Carballo et al., 1997. J Pineal Res 23:97-105), as a regulator of the sleep-wake cycle in general (Burke et al. 2013. Sleep 36:1617-1624) and in patients admitted to Intensive Care Units (Mohan and Brunner, 2005. Acta Anaesthesiol Scand 49:1397). Its intravenous use in newborns with sepsis caused a significant drop in mortality without side effects (Gitto et al., 2004. J Pediatr Surg 39: 184). In this case, melatonin was administered intravenously using an ethanol:water composition (1:50). It has also been demonstrated to have a cardioprotective effect after an acute myocardial infarction (Kücükakin et al., 2008. J Pineal Res 44:426-31). Its ability to reduce the inflammatory response and oxidative stress induced by aggressive procedures during surgery, as well as its safety, efficacy and lack of side effects when administered intravenously at different doses have been demonstrated (Kücükakin et al., 2009. J Surg Res 152:338-347; Naguib et al., 2001. British J Anaesth 90:504-507). In this last reference, the carrier used for administering melatonin is a 2:1:1 mixture of water, propylene glycol (PPG) and 1-methyl-2-pyrrolidone (NMP). Nevertheless, 40 NMP, a widely used solvent, seems essential in this case for solubilizing water-insoluble melatonin. However, the use of NMP as a pharmaceutical carrier is now posing problems due to its reproductive toxicity.

Therefore, in view of the results and of the scientific evidence on the effect, efficacy and safety of the administration of melatonin, it is necessary to produce improved melatonin compositions that exhibit long-term stability and therefore allow storage.

In this regard, international patent application WO2012/156565 discloses a "stable" aqueous melatonin composition comprising 10 mg/ml of propylene glycol. This aqueous composition is stable for 3 months after preparation, but 6 months after preparation, the following characteristics are observed:

The preparation at room temperature, both autoclaved and not autoclaved, has a yellowish appearance, which probably occurs as a result of melatonin oxidation.

The preparation at 4° C., both autoclaved and not autoclaved, crystallizes and does not completely resuspend when at room temperature.

The preparation at −20° C., both autoclaved and not autoclaved, is cloudy and this cloudiness is not successfully eliminated when the preparation is taken to room temperature.

Therefore, preparations of this type do not allow storage periods exceeding 3 months given their scarce long-term stability in all storage conditions described in patent application WO2012/156565. For this reason, the production of improved melatonin compositions that exhibit long-term stability and therefore allow storage exceeding 3 months is still required.

BRIEF DESCRIPTION OF THE INVENTION

The authors of the present invention have developed an aqueous melatonin composition exhibiting surprising long-term stability and allowing high concentrations of said water-insoluble active ingredient. The properties of said composition render it useful as an injectable, for example, for the intravenous administration thereof.

Therefore, a first aspect of the invention relates to a composition comprising propylene glycol, polyethylene glycol also referred to as poly(oxy-1,2-ethyndiyl), alpha-hydro-omega-hydroxy, PEG, Carbowax, poly(ethylene oxide), polyoxyethylene, polyethylene oxide or Macrogol; and melatonin or a derivative, salt, prodrug, or solvate thereof. This type of composition is suitable for preparing injectable compositions of melatonin which are useful, for example, for the intravenous administration thereof. In a preferred embodiment of the first aspect of the invention, this type of composition is lyophilized.

Any polyethylene glycol (hereinafter, PEG) suitable for use in an intramuscularly, subcutaneously or intravenously injectable formulation can be used to carry out the present invention. The PEG will preferably have a molecular weight between 200 and 600 atomic mass units (amu), and more preferably of 400 amu (PEG 400).

PEG (Polyethylene glycol) is a polyether that is widely used in industry and is expressed with the following general formula:

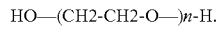

HO—(CH2-CH2-O—)n-H.

It is also known by the name "Macrogol," so PEG400 can also be described as Macrogol 400 and is found as a component in the pharmaceutical industry in drops, injectable solutions, artificial tears, gelatin capsules, etc.

The molecular weight differences between the different types of PEG mean that in addition to giving a "last name" to the type of polyethylene glycol, they have a different presentation and affinity for water. For example, PEG 400 is a colorless viscous liquid with high hygroscopicity close to that of PG, while PEG 6000 is a solid substance with a waxy appearance and low hygroscopicity.

They all have low toxicity, for example the PEG400 LD50 is about 30 g/Kg (oral administration in rats). If the results are extrapolated, for a person weighing 70 kg, the toxic dose would be 2100 g. These characteristics make PEG or macrogol ideal for use as a base material for the solution of the present invention.

A second aspect of the invention relates to a composition comprising water or a saline solution, propylene glycol, polyethylene glycol and melatonin or a derivative, salt, prodrug, or solvate thereof.

A third aspect of the invention relates to the use of the composition described in any of the first or second aspects of the invention in the production of a medicinal product.

A fourth aspect of the invention relates to the composition described in any of the first or second aspects of the invention for use as a medicinal product or for use in therapy.

A fifth aspect of the invention relates to the use of the composition described in any of the first or second aspects of the invention in the production of a medicinal product useful in human subjects for the treatment of circadian rhythm regulation, inflammatory response regulation, the treatment of systemic inflammatory response syndrome (SIRS), the treatment of multiple organ dysfunction syndrome (MODS), the treatment of sepsis in newborns and children; the treatment of sepsis in adults, the treatment of myocardial infarctions, the treatment of mitochondrial damage, the treatment of pulmonary edema, the treatment of kidney or liver failure, or the treatment of an oxidative stress situation generated during surgery, and particularly during abdominal surgery.

An alternative aspect with respect to the fifth aspect of the invention relates to the composition described in any of the first or second aspects of the invention for the treatment in a human subject of circadian rhythm regulation, inflammatory response regulation, the treatment of systemic inflammatory response syndrome (SIRS), the treatment of multiple organ dysfunction syndrome (MODS), the treatment of sepsis in newborns and children; the treatment of sepsis in adults, the treatment of myocardial infarctions, the treatment of mitochondrial damage, the treatment of pulmonary edema, the treatment of kidney or liver failure, or the treatment of an oxidative stress situation generated during surgery, and particularly during abdominal surgery.

In the context of the present invention, an adult human is considered to be patient that is 18 years old or older. A newborn is generally considered to be a patient between 0 and 27 days old, a baby between 28 days and 23 months old, a child from 24 months to 11 years old, and an adolescent from 12 to 17 years old. Although there is a correlation between weight and dose, said correlation is not always linear and must be identified for each group of patients.

The compositions of the invention (see compositions of the first or second aspect of the invention) are prepared using standard methods such as those described or those that are referred to in the Spanish and U.S. Pharmacopoeias and similar reference texts.

A sixth aspect relates to the preparation of the composition of the invention, which comprises mixing water, propylene glycol, polyethylene glycol and melatonin or a derivative, salt, prodrug, or solvate thereof, their salts, prodrugs, derivatives or solvates.

DETAILED DESCRIPTION OF THE INVENTION

The authors have discovered that propylene glycol (PPG) alone without being complemented with the use of co-solvents, many of which are potentially toxic, such as ethanol or NMP, is effective in solubilizing melatonin; however, PPG alone does not allow the production of melatonin compositions exhibiting long-term stability. In that sense, the authors of the present invention have discovered how surprisingly PPG complemented with polyethylene glycol allows not only solubilizing melatonin but also producing compositions exhibiting long-term stability.

Therefore, a first aspect of the invention relates to a composition suitable for being combined with water or a saline solution and for preparing an injectable composition of melatonin comprising propylene glycol, polyethylene glycol and melatonin or a derivative, salt, prodrug, or solvate thereof. In a preferred embodiment of this aspect of the invention, the concentrations of each of the components of the composition of the first aspect of the invention must allow obtaining any of the injectable compositions defined in the second aspect of the invention.

In another preferred embodiment of the first aspect of the invention, the composition is lyophilized and comprises a suitable proportion of each of the following components: propylene glycol, polyethylene glycol and melatonin or a derivative, salt, prodrug, or solvate thereof, in order to be able to obtain, once rehydrated, any of the injectable compositions defined in the second aspect of the invention.

A second aspect of the invention relates to a composition in the form of a pharmaceutically acceptable injectable solution comprising water or a saline solution, propylene glycol, polyethylene glycol and melatonin or a derivative, salt, prodrug, or solvate thereof.

According to a preferred embodiment of the second aspect of the invention, the injectable composition or solution comprises:
  between 5 and 50 grams for every 100 ml of the total solution (w/v) of propylene glycol, preferably between 10 and 30 grams for every 100 ml of the total solution (w/v), more preferably about 20 grams for every 100 ml of the total solution (w/v);
  between 5 and 50 grams for every 100 ml of the total solution (w/v) of polyethylene glycol, preferably between 20 and 40 grams for every 100 ml of the total solution (w/v), more preferably about 30 grams for every 100 ml of the total solution (w/v);
between 0.1 and 30 grams for every 100 ml of the total solution (w/v) of melatonin, preferably between 0.3 and 30 grams for every 100 ml of the total solution (w/v), more preferably between 0.3 and 20 grams for every 100 ml of the total solution (w/v), more preferably between 0.3 and 10 grams for every 100 ml of the total solution (w/v), more preferably between 0.3 and 2 grams for every 100 ml of the total solution (w/v), more preferably between 0.3 and 1 gram for every 100 ml of the total solution (w/v), more preferably between 0.3 and 0.8 grams for every 100 ml of the total solution (w/v) and even more preferably about 0.6 g/100 ml of the total solution; and
a sufficient amount of water or saline solution.

Therefore, the composition described in the second aspect of the invention allows surprisingly high loads of melatonin while at the same time being stable as it was found that at relatively low concentrations of propylene glycol (PPG) used in the present invention, melatonin is significantly solubilized, thereby reducing the risk of irritation or pain which can present as a side effect with the administration of PPG at high concentrations. It is therefore possible to administer high doses of melatonin without administering at the same time large amounts of propylene glycol, which can have toxic effects at very high doses, and in any case reducing the risk of side effects.

The composition of any of the first or second aspects of the invention can also comprise other pharmaceutically acceptable excipients. According to the EMEA's definition, an excipient is considered any component in the composition other than an active ingredient. Examples of excipients that can be used in the injectable composition of the composition include antimicrobial preservatives, such as methylparaben, propylparaben; antioxidants, such as sodium metabisulfite, propyl gallate; stabilizing and suspending agents, such as modified soluble or swellable celluloses, for example sodium carboxymethyl cellulose (Aquasorb, Blanose, Nymcel); tonicity agents, such as sodium chloride; or solubilizers, such as propylene glycol or polyethylene glycols. These excipients must be within the bounds of the definition of the invention.

According to the present invention, a "pharmaceutically acceptable" composition or component thereof indicates that they are physiologically tolerable and the administration thereof entails a low risk of allergies, side effects, adverse events or other similar reactions, such as gastric disorders, dizziness and the like, when administered to a human being. Preferably, as it is used herein, the expression "pharmaceutically acceptable" means that it has been approved by a regulatory agency of the state or federal government or that it is listed in the U.S. Pharmacopoeia or other generally recognized pharmacopoeia for use in animals, and more particularly in human beings. The composition of the invention is therefore pyrogen-free.

The composition of the invention includes melatonin, as well as a derivative, a salt, a prodrug or a solvate thereof. For example, pharmaceutically acceptable salts are synthesized from melatonin by means of conventional chemical methods, generally by making it react with a suitable acid in water or in an organic solvent or in a mixture of both. Non-aqueous media such as ether, ethyl acetate, ethanol, isopropanol or acetonitrile are generally preferred. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate and p-toluenesulfonate.

As it is used in this application, the term "prodrug" is defined herein to mean a chemical compound that has experienced a chemical derivatization, such as a substitution or addition of an additional chemical group to change (for pharmaceutical use) any of its physicochemical properties, such as solubility or bioavailability, for example ester, ether or amide derivatives of an active compound providing the active compound itself after administration to a subject. Those skilled in the art know examples of well-known methods for the production of a prodrug of a given active compound and said methods can be found, for example, in Krogsgaard-Larsen et al., Textbook of Drug Design and Discovery, Taylor & Francis (April 2002).

Particularly preferred prodrugs are those that increase the bioavailability of the compounds of this invention when such compounds are administered to a patient (for example, allowing an orally administered compound to be more readily absorbed into the blood) or that improve the delivery of the original compound to a biological compartment (for example, the brain or lymphatic system) with respect to the original species.

According to this invention, the term "solvate" must be understood to mean any form of melatonin according to the invention having another molecule (most likely a polar solvent) bound by means of a non-covalent bond. The examples of such solvates include hydrates and alcoholates, for example methanolates. The preparation of salts, solvates and prodrugs can be carried out by means of methods known in the art. It must be noted that non-pharmaceutically acceptable salts, solvates or prodrugs are also within the scope of the invention since they can be useful in the preparation of pharmaceutically acceptable salts, solvates or prodrugs.

Various derivatives of melatonin which are also included in the present invention are known in the state of the art. According to a particular embodiment, the derivative of melatonin is defined according to formula (I), a salt, prodrug or solvate thereof

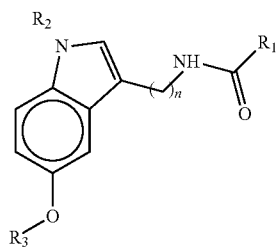

wherein,
n is an integer selected from the group consisting of 1, 2, 3 and 4;
$R_1$ and $R_3$ are selected independently from the group consisting of linear or branched $C_1$-$C_4$ alkyl; and
$R_2$ is selected from the group consisting of hydrogen, linear or branched $C_1$-$C_4$ alkyl, —C(=O)O—Ra and —C(=O)—N(H)—Ra, wherein Ra is a linear or branched $C_1$-$C_4$ alkyl group.

In a particular embodiment, the composition of the invention is intravenously injectable. A particular aspect includes the presence of a second medicinal product in the composition of the invention. Said second medicinal product can be part of the composition or can be provided as a separate composition for the administration at the same time or at different times.

Generally, a "therapeutically effective amount" of the composition of the invention, and therefore of melatonin, will depend on various factors, such as the severity of the disorder being treated, the sex, age or weight of the patient, among many others. For example, the composition of the invention can be administered in the range of 0.1 to 1000 mg/kg/day one or more times a day with standard total daily dosages.

The present invention relates to the use of melatonin, its salts, prodrugs, derivatives or solvates in the preparation of a medicinal product for the treatment in humans or animals of processes such as sepsis, for the treatment of systemic inflammatory response syndrome (SIRS) or for the treatment of multiple organ dysfunction syndrome (MODS), the treatment of myocardial infarctions, the treatment of mitochondrial damage, the treatment of pulmonary edema, the treatment of kidney or liver failure, or the treatment of a surgery-induced oxidative stress situation. In a particular embodiment, said use involves the administration of between 5 and 1,000 mg, between 5 and 700 mg, between 5 and 600 mg or between 5 and 300 mg of melatonin every 24 hours. In another particular embodiment, the amount of melatonin administered to a patient is comprised between 30 and 90 mg every 4 hours, preferably between 40 and 70. In a particular embodiment, between 55 and 75 mg of melatonin are administered to the patient every 24 hours. In general and according to the human equivalent dose calculation (Reagan-Shaw et al. 2007. Faseb J 22:659-661), the minimum doses of melatonin would range between 50 and 500 mg/day (Venegas et al. 2012. J Pineal Res 52:217-227).

In another preferred embodiment of the invention, said use involves the administration of at least 300 mg, preferably at least 400 mg and even more preferably of at least 500 mg of melatonin every 24 hours. In this preferred embodiment of the invention, said use preferably refers to the treatment of sepsis.

In a particular embodiment, the administration is performed by perfusion. In another embodiment, melatonin, its salts, prodrugs, derivatives or solvates, is administered 1, 2, 3, 4, 5 or 6 times or more a day until reaching the required total daily dose. The treatment period can vary according to the patient's progression, and it usually lasts between 1 and 30 days.

In a particular embodiment, said sepsis in adults is severe sepsis. SIRS is a generalized inflammatory response of a range of severe clinical injuries. According to the definition agreed on by the American College of Chest Physicians/Society of Critical Care Medicine, this syndrome is clinically recognized by the presence of two or more of the following symptoms (i) to (iv):

(i) Temperature>38° C. or <36° C.
(ii) Heart rate>90 beats/min.
(iii) Respiratory rate>20 breaths/min or $PaCO_2$<32 mmHg.
(iv) White blood cell count>12,000 cells/$mm_3$, <4,000 cells/$mm_3$, or >10% of immature (band) forms.

Sepsis corresponds to SIRS due to a clear focus of infection. Diagnosis thereof requires two or more SIRS criteria and the presence of a clear clinical picture of infection or microbiological studies (the presence of pathogenic microorganisms in normally sterile fluids, more than 100,000 CFU/ml in urine or in quantitative cultures of bronchial secretions). In addition, sepsis is considered severe when it is associated with organ dysfunction, hypoperfusion or hypotension (<90 mm Hg of systolic blood pressure). Manifestations of hypoperfusion can be included but are not limited to lactic acidosis (lactic acid>3 mmol/l), oliguria (diuresis 50<30 ml/h for 3 hours or 700 ml in 24 hours), coagulopathy (prolongation of the prothrombin time or thrombocytopenia less than 100,000/ml), or an acute change in mental state (agitation, obnubilation).

The term "treatment" or "treating" in the context of this document refers to the administration of a compound or formulation according to the invention to prevent, improve or eradicate the disease or one or more symptoms associated with said disease. "Treatment" also covers the prevention, improvement or eradication of the physiological sequelae of the disease.

Throughout the description and claims the term "comprises" and variants thereof do not seek to exclude other technical characteristics, supplements, components or steps. For the persons skilled in the art, other objects, advantages and features of the invention will be deduced in part from the description and in part from putting the invention into practice.

The following examples and drawings are provided by way of illustration and are not intended to be limiting of the present invention.

EXAMPLES

The invention will be illustrated below by means of tests conducted by the inventors, clearly showing the stability and effectiveness of the composition of the invention.

Example 1. Preparation of the Composition of the Invention

The melatonin for the injectable solution was prepared at a concentration of 6 mg/ml in about 20% of propylene glycol and about 30% of polyethylene glycol and with pyrogen-free water in a sufficient amount (API).

TABLE 1

Qualitative and quantitative composition of the tested composition

| Component | Composition (per ml) | Function |
| --- | --- | --- |
| Melatonin | 6.0 mg | Active ingredient |
| Propylene glycol | 200.0 mg | Excipient |
| Polyethylene glycol (macrogol) | 300.0 mg | Excipient |
| Water for injectables | Sufficient amount 1 ml | Solvent |

The material used for packaging the composition described in Table 1 were type I glass ampoules (EP) previously sterilized in an oven.

Example 2. Stability Tests 2.1. General Principles

The present study is a stability study of the product specified in Table 1 after preparation and over a 6-month period. Three industrial-sized baths each comprising 1,000 ampoules of the product specified in Table 1 were used to that end.

2.2 Stability Test Results

TABLE 2

Long-term stability data containing the solution comprising 6 mg/ml described in Table 1.

Solution comprising 6 mg/ml of melatonin for injection in ampoules.

Batch size: 1,000 ampoules
Manufacturing date: 27 Feb. 2013
Test conditions: Temperature 25° C. +/− 2° C.
Relative Humidity 60% +/− 5%
Position of the product: right
Type of bath: Scaled-down batch
Product container once closed: Type I glass ampoules containing a colorless, clear and particle-free solution.

| Parameter | Technical specifications | 0 (2013/03) | 3 (2013/06) | 6 (2013/06) |
|---|---|---|---|---|
| Appearance of the product | Glass ampoule containing a clear, colorless solution. Particle-free. | Complies with the technical specification | Complies with the technical specification | Complies with the technical specification |
| Identification of melatonin/UV-visible) | Positive | Positive | Positive | Positive |
| Determination of pH | 5.5-7.5 | 6.6 | 6.6 | 6.5 |
| Density | 1.04-1.08 | 1.07 | 1.06 | 1.06 |
| Extractable volume Total | Greater than or equal to 9 mL | 9.5 | 9.4 | 9.3 |
| 5-methoxytryptamine | < or =1.5% | n, d | n, d | 0.11 |
| individual | < or =0.50% | n, d | n, d | n, d |
| unknown degradation products | < or =0.10% | n, d | n, d | |
| TRR0.7 | < or =0.10% | | | 0.01 |
| TRR2.0 | < or =0.10% | | | 0.08 |
| Melatonin content | 5.7-6.5 mg/ml | 5.96 | 5.84 | 5.76 |
| Subvisible particles | >=10 um: < or =6,000 particles/vial | 115 | 135 | 108 |
| | >=25 um: < or =600 particles/vial | 21 | 25 | 18 |
| Tightness | Leak-tight ampoule | Complies with the technical specification | Complies with the technical specification | Complies with the technical specification |
| Bacterial endotoxins (LAL test) | < or =35.1 EU/ml | <35.1 | — | — |
| Sterility test | Sterile | Sterile | — | — |

From the long-term stability test shown, it can be concluded that the described ampoules containing the solution comprising 6 mg/ml of melatonin for injection, after storage over a 6-month period, comply with the technical specifications required for a product having these characteristics.

Example 3. Clinical Study with Septic Patients

The composition of the invention, the solution comprising 6 mg/ml of melatonin for injection in ampoules described in Example 1, hereinafter "injectable of melatonin", was used in a clinical study with 14 septic patients after abdominal surgery randomly distributed into 2 study groups (A and B). Group A corresponds to patients who, in addition to standard treatment, received the injectable of melatonin at a dose of 60 mg/day for 5 days, blood samples being taken daily to perform successive analytical determinations. Treatment group B received standard treatment and placebo, the latter being the same vial with the same excipients but without the melatonin active ingredient; daily blood samples are also obtained from each patient in this group to perform successive analytical determinations. The blood samples are referred to as T0, T1, T2, T3, T4 and T5.

The following blood parameters were analyzed for each of the participating patients from these samples: number of leukocytes, number of red blood cells, hemoglobin, hematocrit, percentage of neutrophils, percentage of lymphocytes, and number of platelets. The biochemical parameters determined in each patient participating in the study were: transaminases (GOT and GPT), gamma-glutamyl transferase, creatinine, urea, alkaline phosphatase (ALP) and lactic dehydrogenase (LDH).

Justification of the Determinations Performed

The blood parameters comprising the number of leukocytes, neutrophils and lymphocytes, as well as the number of platelets, are parameters that are indicative of a septic state. In this regard, sepsis is known to cause a drop in the percentage of lymphocytes.

The determined biochemical parameters are related to liver function, such as:

Glutamate oxalacetate transaminase or aspartate amino transferase (GOT/AST): enzyme belonging to the transaminase group which, by transferring amino groups, catalyzes the conversion of amino acids into corresponding α-oxoacids and vice versa. It is found in the cytoplasm and mitochondria. It is highly specific for a liver disease.

Glutamate pyruvate transaminase or alanine amino transferase (GPT/ALT): enzyme also belonging to the transaminase group and which, by transferring amino groups, catalyzes the conversion of amino acids into corresponding α-oxoacids and vice versa. Its highest level of activity is found in the liver.

Gamma-glutamyl transferase (GGT): contributes to the diagnosis and control of liver-bile diseases. The enzyme activity of GGT is often the only parameter that increases with respect to diseases of this type, and it is highly sensitive.

Alkaline phosphatase (ALP/FA): in the human serum, there are four structural genotypes: liver-bone-kidney type, the intestinal type, the placental type and the stem cell variant. This enzyme is found in osteoblasts, hepatocytes, the kidneys, the spleen, the placenta, the prostate, leukocytes and in the small intestine. The liver-bone-kidney type is of particular importance.

In relation to renal function, the following parameters have been determined:

Creatinine is a waste molecule that is generated from muscle metabolism. Creatinine comes from the creatine, a very important molecule for the production of energy in muscles. About 2% of the body's creatine is converted to creatinine every day. Creatinine is transported from the muscles to the kidney by means of blood. The kidneys filter most of the creatinine and eliminate it in urine. The determination of serum creatinine is a test indicating with fairly accurate reliability the state of renal function.

Urea, the determination of which is the most widely used test to assess renal function. Urea is the end product of protein and amino acid metabolism. In protein degradation, proteins are broken down into amino acids and deaminated. With the ammonia that is formed, urea is synthesized in the liver. This is the most important pathway in the human body for excess nitrogen degradation.

To detect lesions in tissues such as the liver, the enzyme lactate dehydrogenase (also called "lactic acid dehydrogenase" (LDH)) an enzyme which is found in virtually all tissues in the human body, has been determined. It plays an important role in cellular respiration (the process in which the glucose coming from foods is turned into energy that can be used by cells).

Even if LDH is abundant in tissue cells, blood levels are generally low. However, when tissues become damaged due to a lesion or disease, they release more LDH into the blood stream. The conditions usually causing this increase in the amount of LDH in the blood stream are the following: liver diseases, heart attacks, anemia, muscle trauma, bone fractures, cancer, infections such as meningitis, encephalitis or HIV.

Results and Discussion

The data from the study has been statistically analyzed by an independent statistician and the following results are obtained:

Leukocytes: The results show a decline in the leukocyte levels both in group A and group B; although leukocyte values decline on average in both groups, the differences are not statistically significant.

Red blood cells: Although red blood cell values decline on average in both groups, the differences are not statistically significant.

Hemoglobin: Although hemoglobin values decline on average in both groups, the differences are not statistically significant.

Hematocrit: Although hematocrit values decline on average in both groups, the differences are not statistically significant.

Platelets: Although platelet values increase on average in both groups, the differences are not statistically significant.

Lymphocytes: There are significant differences between the groups (p=0.015), i.e., the lymphocyte average is greater in group A (treated with the injectable of melatonin) than in group B (placebo), regardless of the time (the differences are the same at all measured moments). Furthermore, the effect of time is statistically significant (p=0.005, since sphericity is not complied with), which means that the increase in lymphocyte levels is different at the different measured moments in time. Specifically, the differences are due to times 4 and 5 with respect to the initial time.

Neutrophils: Like in the case of lymphocytes, there are significant differences between the study groups (p=0.007), i.e., the neutrophil average is greater in group B (placebo) than in group A (melatonin), regardless of the time (the differences are the same at all measured moments). The differences over time are statistically significant (p=0.042, since sphericity is not complied with). It can virtually be said that after moment 3, the decline starts to be significant in group A (melatonin).

GOT: Even though initial GOT levels are higher in patients subjected to treatment (group A), the differences in average values are not statistically significant (p=0.633). Nor is the change in the different moments in time significant, i.e., GOT levels remain virtually identical.

GPT: The change in GPT levels is not significant in the different measured moments. Nor are the average values statistically significant.

GGT: The change in GGT levels is not significant in the different measured moments. Nor are the average values statistically significant.

ALP (alkaline phosphatase): The change in alkaline phosphatase is not significant in the different measured moments. Nor are the average values statistically significant.

Urea: There are no significant differences in urea levels over time; they remain virtually identical in both groups (Friedman test, p=0.205 for group A and p=0.959 for group B). If urea levels between the two groups are compared at each measured moment in time, it can be seen that urea levels are higher in group B (placebo) at all the measured moments (except the last one). The differences are statistically significant.

Creatinine: There are no significant differences in creatinine levels over time; they remain identical in both groups (Friedman test, p=0.122 for group A and p=0.831 for group B). If creatinine levels between the two groups are compared at each measured moment in time, it can be seen that there are no statistically significant differences in creatinine levels between groups A and B.

LDH: There are no significant differences in LDH levels over time; they remain virtually identical in both groups (Friedman test, p=0.355 for group A and p=0.921 for group B). If LDH levels between the two groups are compared at each measured moment in time, it can be seen that LDH levels are higher in group A (melatonin) at all the measured times, although the differences are not statistically significant.

Analyses with Non-Parametric Tests:

Even though the hypothesis of normality of all the variables is complied with despite the small sample size, non-parametric tests were used as they are more robust and suitable when the samples are so small.

Taking this into account, on one hand the progression over time of the different parameters in each group have been compared separately using the Friedman test for independent samples. For progression over time, statistically significant differences (p<0.10) are obtained in the following parameters:

The hemoglobin level observed at different times for group A (p=0.069).

The platelet level observed at different times for group A (p=0.056) and B (p=0.069).

The lymphocyte level observed at different times for group A (p=0.030) and B (p=0.085).

The neutrophil level observed at different times for group A (p=0.070).

The GOT level observed at different times for group A (p=0.013) and B (p=0.077).

The GPT level observed at different times for group B (p=0.004).

The GGT level observed at different times for group A (p=0.079).

In addition, the direct differences between groups A and B have been compared at each moment in time independently using the Mann-Whitney test for independent samples, giving the following results:

At moment T2, there are differences between A and B in red blood cell (p=0.026), hemoglobin (p=0.038) and hematocrit (p=0.053) levels.

There are differences in lymphocyte levels at all times.

There are differences in neutrophil levels between A and B at T2 (p=0.007) and T3 (p=0.011).

There are differences in GPT levels between A and B at T5 (p=0.038).

CONCLUSIONS

Treatment with the injectable of melatonin in septic patients in group A receiving the injectable shows a progressive increase in the percentage of lymphocytes. This increase is statistically significant. These patients also show a statistically significant decline in the percentage of neutrophils. Both the increase in lymphocytes and the decline in neutrophils occur at all times of the study, reaching levels close to normal values in healthy individuals at the end of the study period. This situation entails an immunological recovery in patients receiving treatment with the injectable of melatonin, as the balance between lymphocytes and neutrophils in patients receiving treatment with the injectable is achieved.

In addition, treatment with the injectable of melatonin does not involve any liver or kidney damage in patients receiving treatment with the injectable.

Statistical Analysis Details

The details of the analysis performed on the parameters measured at all the moments (T0, . . . , T5) of the study are provided below.

Leukocytes

|  | Group | Mean | Standard Deviation | N |
| --- | --- | --- | --- | --- |
| Leukocytes 10_3 ml T0 | A | 14.7329 | 9.09637 | 7 |
|  | B | 19.2857 | 7.82250 | 7 |
|  | Total | 17.0093 | 8.48601 | 14 |
| Leukocytes 10_3 ml T1 | A | 14.4200 | 9.59540 | 7 |
|  | B | 19.0529 | 8.86479 | 7 |
|  | Total | 16.7364 | 9.19473 | 14 |
| Leukocytes 10_3 ml T2 | A | 11.6614 | 4.49294 | 7 |
|  | B | 16.6786 | 5.94305 | 7 |
|  | Total | 14.1700 | 5.69169 | 14 |
| Leukocytes 10_3 ml T3 | A | 10.1457 | 4.71706 | 7 |
|  | B | 15.5086 | 5.02559 | 7 |
|  | Total | 12.8271 | 5.44697 | 14 |
| Leukocytes 10_3 ml T4 | A | 11.9529 | 8.60995 | 7 |
|  | B | 15.4971 | 3.56829 | 7 |
|  | Total | 13.7250 | 6.59341 | 14 |
| Leukocytes 10_3 ml T5 | A | 12.1114 | 6.91874 | 7 |
|  | B | 12.8900 | 2.85623 | 7 |
|  | Total | 12.5007 | 5.10116 | 14 |

Although leukocyte values decline on average in both groups, the differences are not statistically significant.

Red Blood Cells

|  | Group | Mean | Standard Deviation | N |
| --- | --- | --- | --- | --- |
| red blood cells 10_3 ml T0 | A | 4.1243 | 0.83320 | 7 |
|  | B | 3.4043 | 1.06878 | 7 |
|  | Total | 3.7643 | 0.99358 | 14 |
| red blood cells 10_3 ml T1 | A | 3.8457 | 0.62612 | 7 |
|  | B | 3.7671 | 0.74904 | 7 |
|  | Total | 3.8064 | 0.66449 | 14 |
| red blood cells 10_3 ml T2 | A | 3.8100 | 0.32655 | 7 |
|  | B | 3.1486 | 0.64300 | 7 |
|  | Total | 3.4793 | 0.59818 | 14 |
| red blood cells 10_3 ml T3 | A | 3.6071 | 0.31700 | 7 |
|  | B | 3.2843 | 0.49315 | 7 |
|  | Total | 3.4457 | 0.43207 | 14 |
| red blood cells 10_3 ml T4 | A | 3.6371 | 0.52506 | 7 |
|  | B | 3.4357 | 0.56151 | 7 |
|  | Total | 3.5364 | 0.53262 | 14 |
| red blood cells 10_3 ml T5 | A | 3.6900 | 0.52173 | 7 |
|  | B | 3.2643 | 0.66795 | 7 |
|  | Total | 3.4771 | 0.61672 | 14 |

Although red blood cell values decline on average in both groups, the differences are not statistically significant.

Hemoglobin

|  | Group | Mean | Standard Deviation | N |
| --- | --- | --- | --- | --- |
| hemoglobin 10_3 ml T0 | A | 12.0714 | 2.59597 | 7 |
|  | B | 10.1143 | 2.72484 | 7 |
|  | Total | 11.0929 | 2.75107 | 14 |

-continued

|  | Group | Mean | Standard Deviation | N |
|---|---|---|---|---|
| hemoglobin 10_3 ml T1 | A | 11.0857 | 1.94202 | 7 |
|  | B | 11.3143 | 1.88275 | 7 |
|  | Total | 11.2000 | 1.84140 | 14 |
| hemoglobin 10_3 ml T2 | A | 11.0571 | 0.85021 | 7 |
|  | B | 9.4143 | 1.63649 | 7 |
|  | Total | 10.2357 | 1.51536 | 14 |
| hemoglobin 10_3 ml T3 | A | 10.6429 | 1.01301 | 7 |
|  | B | 9.8143 | 1.15243 | 7 |
|  | Total | 10.2286 | 1.12758 | 14 |
| hemoglobin 10_3 ml T4 | A | 10.6143 | 1.37408 | 7 |
|  | B | 10.1429 | 1.28693 | 7 |
|  | Total | 10.3786 | 1.30217 | 14 |
| hemoglobin 10_3 ml T5 | A | 10.7286 | 1.52065 | 7 |
|  | B | 9.5143 | 1.54103 | 7 |
|  | Total | 10.1214 | 1.60009 | 14 |

Although hemoglobin values decline on average in both groups, the differences are not statistically significant.

Hematocrit

|  | Group | Mean | Standard Deviation | N |
|---|---|---|---|---|
| hematocrit (%) T0 | A | 34.2857 | 7.21097 | 7 |
|  | B | 29.4714 | 8.19445 | 7 |
|  | Total | 31.8786 | 7.82503 | 14 |
| hematocrit (%) T1 | A | 32.1143 | 5.31583 | 7 |
|  | B | 32.9571 | 5.82662 | 7 |
|  | Total | 32.5357 | 5.37610 | 14 |
| hematocrit (%) T2 | A | 31.9714 | 2.38447 | 7 |
|  | B | 27.6143 | 5.00447 | 7 |
|  | Total | 29.7929 | 4.39256 | 14 |
| hematocrit (%) T3 | A | 30.3857 | 2.65796 | 7 |
|  | B | 28.7143 | 3.62971 | 7 |
|  | Total | 29.5500 | 3.17702 | 14 |
| hematocrit (%) T4 | A | 30.6571 | 4.25435 | 7 |
|  | B | 30.0571 | 3.99452 | 7 |
|  | Total | 30.3571 | 3.97680 | 14 |
| hematocrit (%) T5 | A | 31.1143 | 4.22588 | 7 |
|  | B | 28.5714 | 5.12826 | 7 |
|  | Total | 29.8429 | 4.70331 | 14 |

Although hematocrit values decline on average in both groups, the differences are not statistically significant.

Platelets

|  | Group | Mean | Standard Deviation | N |
|---|---|---|---|---|
| platelets 10_3 ml T0 | A | 249.0000 | 165.65526 | 7 |
|  | B | 387.7143 | 215.01451 | 7 |
|  | Total | 318.3571 | 197.94778 | 14 |
| platelets 10_3 ml T1 | A | 234.4286 | 183.64355 | 7 |
|  | B | 374.5714 | 229.87958 | 7 |
|  | Total | 304.5000 | 212.70375 | 14 |
| platelets 10_3 ml T2 | A | 240.2857 | 196.55594 | 7 |
|  | B | 316.8571 | 194.91146 | 7 |
|  | Total | 278.5714 | 192.20771 | 14 |
| platelets 10_3 ml T3 | A | 256.1429 | 187.80879 | 7 |
|  | B | 301.7143 | 213.66930 | 7 |
|  | Total | 278.9286 | 194.70469 | 14 |
| platelets 10_3 ml T4 | A | 317.7143 | 250.15576 | 7 |
|  | B | 320.8571 | 201.71880 | 7 |
|  | Total | 319.2857 | 218.32313 | 14 |
| platelets 10_3 ml T5 | A | 380.1429 | 309.16847 | 7 |
|  | B | 277.7143 | 220.31017 | 7 |
|  | Total | 328.9286 | 263.32941 | 14 |

Although platelet values increase on average in both groups, the differences are not statistically significant.

Lymphocytes

|  | Group | Mean | Standard Deviation | N |
|---|---|---|---|---|
| lymphocytes 10_3 ml T0 | A | 7.9571 | 3.79599 | 7 |
|  | B | 4.8286 | 2.78132 | 7 |
|  | Total | 6.3929 | 3.58554 | 14 |
| lymphocytes (%) T1 | A | 8.9571 | 5.23159 | 7 |
|  | B | 4.6714 | 1.12207 | 7 |
|  | Total | 6.8143 | 4.26125 | 14 |
| lymphocytes (%) T2 | A | 11.9714 | 5.03545 | 7 |
|  | B | 5.6143 | 2.59257 | 7 |
|  | Total | 8.7929 | 5.06807 | 14 |
| lymphocytes (%) T3 | A | 14.3571 | 7.43928 | 7 |
|  | B | 5.5714 | 2.36130 | 7 |
|  | Total | 9.9643 | 6.99270 | 14 |
| lymphocytes (%) T4 | A | 16.6143 | 11.13903 | 7 |
|  | B | 7.4143 | 3.56718 | 7 |
|  | Total | 12.0143 | 9.26971 | 14 |
| lymphocytes (%) T5 | A | 17.1571 | 9.21590 | 7 |
|  | B | 8.2571 | 5.01825 | 7 |
|  | Total | 12.7071 | 8.49402 | 14 |

Tests of within-Subject Effects

Transformed Variable: Average

| Source | Type III Sum of Squares | df | Mean Square | F | Sig. |
|---|---|---|---|---|---|
| Intercept | 7497.630 | 1 | 7497.630 | 62.512 | 0.000 |
| Group | 964.252 | 1 | 964.252 | 8.040 | 0.015 |
| Error | 1439.268 | 12 | 119.939 |  |  |

There are significant differences between groups ($p=0.015$), i.e., the lymphocyte average is greater in group A than in group B, regardless of the time (the differences are the same at all measured moments).

Furthermore, the effect of time is statistically significant ($p=0.005$, since sphericity is not complied with), which means that the increase in lymphocyte levels is different at the different measured moments in time.

Specifically, the differences are due to times 4 and 5 with respect to the initial time:

Tests of within-Subject Effects

| Source | | Type III Sum of Squares | df | Mean Square | F | Sig. |
|---|---|---|---|---|---|---|
| time | Sphericity assumed | 478.435 | 5 | 95.687 | 6.345 | 0.000 |
| | Greenhouse-Geisser | 478.435 | 2.190 | 218.472 | 6.345 | 0.005 |
| | Huynh-Feldt | 478.435 | 2.921 | 163.772 | 6.345 | 0.002 |
| | Lower-bound | 478.435 | 1.000 | 478.435 | 6.345 | 0.027 |
| time * Group | Sphericity assumed | 119.374 | 5 | 23.875 | 1.583 | 0.179 |
| | Greenhouse-Geisser | 119.374 | 2.190 | 54.511 | 1.583 | 0.223 |
| | Huynh-Feldt | 119.374 | 2.921 | 40.862 | 1.583 | 0.212 |
| | Lower-bound | 119.374 | 1.000 | 119.374 | 1.583 | 0.232 |
| Error(time) | Sphericity assumed | 904.861 | 60 | 15.081 | | |
| | Greenhouse-Geisser | 904.861 | 26.279 | 34.433 | | |
| | Huynh-Feldt | 904.861 | 35.056 | 25.812 | | |
| | Lower-bound | 904.861 | 12.000 | 75.405 | | |

Tests of within-Subject Contrasts

| Source | Time | Type III Sum of Squares | df | Mean Square | F | Sig. |
|---|---|---|---|---|---|---|
| time | Level 2 with respect to level 1 | 2.486 | 1 | 2.486 | 0.119 | 0.736 |
| | Level 3 with respect to level 1 | 80.640 | 1 | 80.640 | 4.410 | 0.058 |
| | Level 4 with respect to level 1 | 178.571 | 1 | 178.571 | 4.678 | 0.051 |
| | Level 5 with respect to level 1 | 442.406 | 1 | 442.406 | 6.974 | 0.022 |
| | Level 6 with respect to level 1 | 558.183 | 1 | 558.183 | 8.240 | 0.014 |
| time * Group | Level 2 with respect to level 1 | 4.686 | 1 | 4.686 | 0.225 | 0.644 |
| | Level 3 with respect to level 1 | 36.483 | 1 | 36.483 | 1.995 | 0.183 |
| | Level 4 with respect to level 1 | 112.011 | 1 | 112.011 | 2.934 | 0.112 |
| | Level 5 with respect to level 1 | 129.018 | 1 | 129.018 | 2.034 | 0.179 |
| | Level 6 with respect to level 1 | 116.583 | 1 | 116.583 | 1.721 | 0.214 |
| Error(time) | Level 2 with respect to level 1 | 249.977 | 12 | 20.831 | | |
| | Level 3 with respect to level 1 | 219.437 | 12 | 18.286 | | |
| | Level 4 with respect to level 1 | 458.117 | 12 | 38.176 | | |
| | Level 5 with respect to level 1 | 761.286 | 12 | 63.440 | | |
| | Level 6 with respect to level 1 | 812.914 | 12 | 67.743 | | |

Neutrophils

| | Group | Mean | Standard Deviation | N |
|---|---|---|---|---|
| neutrophils (%) T0 | A | 87.1143 | 6.82799 | 7 |
| | B | 92.4286 | 5.35435 | 7 |
| | Total | 89.7714 | 6.50792 | 14 |
| neutrophils (%) T1 | A | 86.3143 | 8.33175 | 7 |
| | B | 92.2714 | 2.84413 | 7 |
| | Total | 89.2929 | 6.73252 | 14 |
| neutrophils (%) T2 | A | 81.2143 | 6.01953 | 7 |
| | B | 90.6429 | 4.01325 | 7 |
| | Total | 85.9286 | 6.93480 | 14 |
| neutrophils (%) T3 | A | 79.0714 | 8.00411 | 7 |
| | B | 91.7571 | 3.77618 | 7 |
| | Total | 85.4143 | 8.91497 | 14 |
| neutrophils (%) T4 | A | 77.8143 | 12.25988 | 7 |
| | B | 87.7857 | 6.93023 | 7 |
| | Total | 82.8000 | 10.87693 | 14 |
| neutrophils (%) T5 | A | 76.7286 | 12.21757 | 7 |
| | B | 87.9571 | 6.84930 | 7 |
| | Total | 82.3429 | 11.15752 | 14 |

Like in the preceding case, there are significant differences between groups (p=0.007), i.e., the neutrophil average is greater in group B than in group A, regardless of the time (the differences are the same at all measured moments).

Tests of within-Subject Effects

Transformed Variable: Average

| Source | Type III Sum of Squares | df | Mean Square | F | Sig. |
|---|---|---|---|---|---|
| Intercept | 103363.479 | 1 | 103363.479 | 3804.053 | 0.000 |
| Group | 289.683 | 1 | 289.683 | 10.661 | 0.007 |
| Error | 326.063 | 12 | 27.172 | | |

The differences over time are statistically significant (p=0.042, since sphericity is not complied with). It can virtually be said that after moment 3, the decline starts to be significant.

Tests of within-Subject Effects

| Source | | Type III Sum of Squares | df | Mean Square | F | Sig. |
|---|---|---|---|---|---|---|
| time | Sphericity assumed | 685.940 | 5 | 137.188 | 3.898 | 0.004 |
| | Greenhouse-Geisser | 685.940 | 1.725 | 397.654 | 3.898 | 0.042 |
| | Huynh-Feldt | 685.940 | 2.156 | 318.204 | 3.898 | 0.030 |
| | Lower-bound | 685.940 | 1.000 | 685.940 | 3.898 | 0.072 |
| time * Group | Sphericity assumed | 148.626 | 5 | 29.725 | 0.845 | 0.524 |
| | Greenhouse-Geisser | 148.626 | 1.725 | 86.162 | 0.845 | 0.428 |
| | Huynh-Feldt | 148.626 | 2.156 | 68.947 | 0.845 | 0.449 |
| | Lower-bound | 148.626 | 1.000 | 148.626 | 0.845 | 0.376 |
| Error(time) | Sphericity assumed | 2111.492 | 60 | 35.192 | | |
| | Greenhouse-Geisser | 2111.492 | 20.700 | 102.007 | | |
| | Huynh-Feldt | 2111.492 | 25.868 | 81.626 | | |
| | Lower-bound | 2111.492 | 12.000 | 175.958 | | |

Tests of within-Subject Contrast

| Source | Time | Type III Sum of Squares | df | Mean Square | F | Sig. |
|---|---|---|---|---|---|---|
| time | Level 2 with respect to level 1 | 3.206 | 1 | 3.206 | 0.073 | 0.791 |
| | Level 3 with respect to level 1 | 206.746 | 1 | 206.746 | 14.423 | 0.003 |
| | Level 4 with respect to level 1 | 265.786 | 1 | 265.786 | 3.255 | 0.096 |
| | Level 5 with respect to level 1 | 680.411 | 1 | 680.411 | 4.826 | 0.048 |
| | Level 6 with respect to level 1 | 772.571 | 1 | 772.571 | 4.499 | 0.055 |
| time * Group | Level 2 with respect to level 1 | 1.446 | 1 | 1.446 | 0.033 | 0.859 |
| | Level 3 with respect to level 1 | 59.246 | 1 | 59.246 | 4.133 | 0.065 |
| | Level 4 with respect to level 1 | 190.183 | 1 | 190.183 | 2.329 | 0.153 |
| | Level 5 with respect to level 1 | 75.911 | 1 | 75.911 | 0.538 | 0.477 |
| | Level 6 with respect to level 1 | 122.426 | 1 | 122.426 | 0.713 | 0.415 |
| Error(time) | Level 2 with respect to level 1 | 525.577 | 12 | 43.798 | | |
| | Level 3 with respect to level 1 | 172.009 | 12 | 14.334 | | |
| | Level 4 with respect to level 1 | 979.811 | 12 | 81.651 | | |
| | Level 5 with respect to level 1 | 1691.737 | 12 | 140.978 | | |
| | Level 6 with respect to level 1 | 2060.663 | 12 | 171.722 | | |

GOT

| | Group | Mean | Standard Deviation | N |
|---|---|---|---|---|
| GOT T0 | A | 65.1667 | 51.40201 | 6 |
| | B | 27.9500 | 25.27795 | 6 |
| | Total | 46.5583 | 43.23398 | 12 |
| GOT T1 | A | 56.3333 | 48.38457 | 6 |
| | B | 38.8333 | 22.24785 | 6 |
| | Total | 47.5833 | 37.04901 | 12 |
| GOT T2 | A | 41.0000 | 41.26984 | 6 |
| | B | 45.6667 | 53.67184 | 6 |
| | Total | 43.3333 | 45.71121 | 12 |
| GOT T3 | A | 38.3333 | 34.93232 | 6 |
| | B | 35.0333 | 24.83881 | 6 |
| | Total | 36.6833 | 28.94954 | 12 |
| GOT T4 | A | 38.1667 | 35.92446 | 6 |
| | B | 40.7667 | 33.31556 | 6 |
| | Total | 39.4667 | 33.06020 | 12 |
| GOT T5 | A | 44.8333 | 48.67614 | 6 |
| | B | 35.2500 | 29.48856 | 6 |
| | Total | 40.0417 | 38.69488 | 12 |

Even though initial GOT levels are higher in patients in treatment A, the differences in average values are not statistically significant (p=0.633). Nor is the change at the different moments in time significant, i.e., GOT levels remain virtually identical.

Tests of within-Subject Effects

Transformed Variable: Average

| Source | Type III Sum of Squares | df | Mean Square | F | Sig. |
|---|---|---|---|---|---|
| Intercept | 21448.926 | 1 | 21448.926 | 17.157 | 0.002 |
| Group | 303.343 | 1 | 303.343 | 0.243 | 0.633 |
| Error | 12501.881 | 10 | 1250.188 | | |

GPT

| | Group | Mean | Standard Deviation | N |
|---|---|---|---|---|
| GPT T0 | A | 51.0000 | 54.22791 | 7 |
| | B | 15.7167 | 9.56147 | 6 |
| | Total | 34.7154 | 42.93710 | 13 |
| GPT T1 | A | 45.0000 | 46.54747 | 7 |
| | B | 25.5000 | 18.09696 | 6 |
| | Total | 36.0000 | 36.36161 | 13 |

|  | Group | Mean | Standard Deviation | N |
|---|---|---|---|---|
| GPT T2 | A | 40.2857 | 29.78654 | 7 |
|  | B | 24.0000 | 12.69646 | 6 |
|  | Total | 32.7692 | 24.12866 | 13 |
| GPT T3 | A | 32.7143 | 21.06114 | 7 |
|  | B | 17.7500 | 7.27839 | 6 |
|  | Total | 25.8077 | 17.43982 | 13 |
| GPT T4 | A | 30.5714 | 19.26012 | 7 |
|  | B | 17.6000 | 7.75113 | 6 |
|  | Total | 24.5846 | 15.99405 | 13 |
| GPT T5 | A | 30.2857 | 21.47645 | 7 |
|  | B | 13.6667 | 6.59293 | 6 |
|  | Total | 22.6154 | 17.97470 | 13 |

The change in GPT levels is not significant in the different measured moments. Nor are the average values statistically significant.

GGT

|  | Group | Mean | Standard Deviation | N |
|---|---|---|---|---|
| GGT T0 | A | 150.2857 | 158.16206 | 7 |
|  | B | 94.9333 | 50.15283 | 6 |
|  | Total | 124.7385 | 119.91896 | 13 |
| GGT T1 | A | 131.7143 | 144.03786 | 7 |
|  | B | 94.6667 | 53.64202 | 6 |
|  | Total | 114.6154 | 109.27911 | 13 |
| GGT T2 | A | 130.2857 | 140.32904 | 7 |
|  | B | 82.3333 | 35.61835 | 6 |
|  | Total | 108.1538 | 104.85136 | 13 |
| GGT T3 | A | 142.4286 | 160.26526 | 7 |
|  | B | 128.0000 | 94.47963 | 6 |
|  | Total | 135.7692 | 128.91027 | 13 |
| GGT T4 | A | 147.7143 | 134.40575 | 7 |
|  | B | 211.5000 | 186.63735 | 6 |
|  | Total | 177.1538 | 156.97709 | 13 |
| GGT T5 | A | 240.8571 | 204.12858 | 7 |
|  | B | 194.5000 | 194.53611 | 6 |
|  | Total | 219.4615 | 192.82445 | 13 |

The change in GGT levels is not significant in the different measured moments. Nor are the average values statistically significant.

Alkaline Phosphatase

|  | Group | Mean | Standard Deviation | N |
|---|---|---|---|---|
| Phosphatase T0 | A | 116.6667 | 87.96969 | 6 |
|  | B | 95.0000 | 22.47665 | 6 |
|  | Total | 105.8333 | 62.25145 | 12 |
| Phosphatase T1 | A | 100.5000 | 87.36761 | 6 |
|  | B | 84.0000 | 30.02665 | 6 |
|  | Total | 92.2500 | 62.87813 | 12 |
| Phosphatase T2 | A | 97.0000 | 54.85618 | 6 |
|  | B | 74.8333 | 16.40020 | 6 |
|  | Total | 85.9167 | 40.29992 | 12 |
| Phosphatase T3 | A | 106.3333 | 65.98081 | 6 |
|  | B | 109.1667 | 70.30339 | 6 |
|  | Total | 107.7500 | 65.02045 | 12 |
| Phosphatase T4 | A | 108.8333 | 54.57258 | 6 |
|  | B | 159.3333 | 118.81021 | 6 |
|  | Total | 134.0833 | 92.00836 | 12 |
| Phosphatase T5 | A | 112.1667 | 43.56336 | 6 |
|  | B | 143.8333 | 102.89104 | 6 |
|  | Total | 128.0000 | 77.12446 | 12 |

The change in alkaline phosphatase is not significant in the different measured moments. Nor are the average values statistically significant.

Analyses with Non-Parametric Tests:

On one hand, the progression over time of the different parameters in each group is compared separately (using the Friedman test for independent samples), statistically significant differences ($p<0.10$) are obtained in:

The hemoglobin level observed at different times for group A ($p=0.069$):

| Group |  |  | hemoglobin 10_3 ml T0 | hemoglobin 10_3 ml T1 | hemoglobin 10_3 ml T2 | hemoglobin 10_3 ml T3 | hemoglobin 10_3 ml T4 | hemoglobin 10_3 ml T5 |
|---|---|---|---|---|---|---|---|---|
| A | N | Valid | 7 | 7 | 7 | 7 | 7 | 7 |
|  |  | Lost | 0 | 0 | 0 | 0 | 0 | 0 |
|  |  | Mean | 12.0714 | 11.0857 | 11.0571 | 10.6429 | 10.6143 | 10.7286 |
|  |  | Median | 12.3000 | 11.4000 | 11.0000 | 10.7000 | 10.3000 | 10.9000 |
|  |  | SD | 2.59597 | 1.94202 | .85021 | 1.01301 | 1.37408 | 1.52065 |
|  |  | Minimum | 7.40 | 6.90 | 9.50 | 8.80 | 9.20 | 8.40 |
|  |  | Maximum | 16.10 | 12.90 | 12.30 | 11.50 | 13.30 | 13.00 |
| B | N | Valid | 7 | 7 | 7 | 7 | 7 | 7 |
|  |  | Lost | 0 | 0 | 0 | 0 | 0 | 0 |
|  |  | Mean | 10.1143 | 11.3143 | 9.4143 | 9.8143 | 10.1429 | 9.5143 |
|  |  | Median | 9.1000 | 11.1000 | 9.0000 | 9.9000 | 10.0000 | 9.6000 |
|  |  | SD | 2.72484 | 1.88275 | 1.63649 | 1.15243 | 1.28693 | 1.54103 |
|  |  | Minimum | 8.40 | 8.60 | 7.60 | 8.70 | 8.80 | 7.40 |
|  |  | Maximum | 16.10 | 14.10 | 12.50 | 11.90 | 12.30 | 11.40 |

The platelet level observed at different times for groups A (p=0.056) and B (p=0.069):

| | Group | | platelets 10_3 ml T0 | platelets 10_3 ml T1 | platelets 10_3 ml T2 | platelets 10_3 ml T3 | platelets 10_3 ml T4 | platelets 10_3 ml T5 |
|---|---|---|---|---|---|---|---|---|
| A | N | Valid | 7 | 7 | 7 | 7 | 7 | 7 |
| | | Lost | 0 | 0 | 0 | 0 | 0 | 0 |
| | Mean | | 249.0000 | 234.4286 | 240.2857 | 256.1429 | 317.7143 | 380.1429 |
| | Median | | 205.0000 | 147.0000 | 152.0000 | 185.0000 | 220.0000 | 269.0000 |
| | SD | | 165.65526 | 183.64355 | 196.55594 | 187.80879 | 250.15576 | 309.16847 |
| | Minimum | | 87.00 | 44.00 | 33.00 | 33.00 | 59.00 | 97.00 |
| | Maximum | | 521.00 | 558.00 | 578.00 | 549.00 | 784.00 | 963.00 |
| B | N | Valid | 7 | 7 | 7 | 7 | 7 | 7 |
| | | Lost | 0 | 0 | 0 | 0 | 0 | 0 |
| | Mean | | 387.7143 | 374.5714 | 316.8571 | 301.7143 | 320.8571 | 277.7143 |
| | Median | | 350.0000 | 243.0000 | 185.0000 | 195.0000 | 267.0000 | 196.0000 |
| | SD | | 215.01451 | 229.87958 | 194.91146 | 213.66930 | 201.71880 | 220.31017 |
| | Minimum | | 163.00 | 155.00 | 149.00 | 67.00 | 61.00 | 37.00 |
| | Maximum | | 635.00 | 738.00 | 595.00 | 638.00 | 611.00 | 607.00 |

The lymphocyte level observed at different times for groups A (p=0.030) and B (p=0.085):

| | Group | | | lymphocytes 10_3 ml T0 | lymphocytes (%) T1 | lymphocytes (%) T2 | lymphocytes (%) T3 | lymphocytes (%) T4 | lymphocytes (%) T5 |
|---|---|---|---|---|---|---|---|---|---|
| A | N | Valid | | 7 | 7 | 7 | 7 | 7 | 7 |
| | | Lost | | 0 | 0 | 0 | 0 | 0 | 0 |
| | Mean | | | 7.9571 | 8.9571 | 11.9714 | 14.3571 | 16.6143 | 17.1571 |
| | Median | | | 7.2000 | 8.2000 | 11.0000 | 11.9000 | 12.5000 | 15.3000 |
| | SD | | | 3.79599 | 5.23159 | 5.03545 | 7.43928 | 11.13903 | 9.21590 |
| | Minimum | | | 3.00 | 2.70 | 4.50 | 2.80 | 2.60 | 5.40 |
| | Maximum | | | 13.40 | 18.90 | 18.20 | 24.60 | 36.60 | 29.70 |
| | Percentiles | 25 | | 4.3000 | 5.2000 | 8.0000 | 10.6000 | 11.5000 | 9.7000 |
| | | 50 | | 7.2000 | 8.2000 | 11.0000 | 11.9000 | 12.5000 | 15.3000 |
| | | 75 | | 12.1000 | 10.8000 | 17.2000 | 20.6000 | 25.6000 | 27.1000 |
| B | N | Valid | | 7 | 7 | 7 | 7 | 7 | 7 |
| | | Lost | | 0 | 0 | 0 | 0 | 0 | 0 |
| | Mean | | | 4.8286 | 4.6714 | 5.6143 | 5.5714 | 7.4143 | 8.2571 |
| | Median | | | 3.9000 | 5.2000 | 4.9000 | 5.4000 | 5.8000 | 7.7000 |
| | SD | | | 2.78132 | 1.12207 | 2.59257 | 2.36130 | 3.56718 | 5.01825 |
| | Minimum | | | 3.30 | 2.60 | 3.10 | 2.20 | 4.30 | 2.00 |
| | Maximum | | | 11.10 | 5.70 | 10.30 | 9.40 | 14.10 | 17.90 |
| | Percentiles | 25 | | 3.5000 | 3.9000 | 3.8000 | 4.3000 | 4.6000 | 4.5000 |
| | | 50 | | 3.9000 | 5.2000 | 4.9000 | 5.4000 | 5.8000 | 7.7000 |
| A | N | Valid | | 7 | 7 | 7 | 7 | 7 | 7 |
| | | Lost | | 0 | 0 | 0 | 0 | 0 | 0 |
| | Mean | | | 7.9571 | 8.9571 | 11.9714 | 14.3571 | 16.6143 | 17.1571 |
| | Median | | | 7.2000 | 8.2000 | 11.0000 | 11.9000 | 12.5000 | 15.3000 |
| | SD | | | 3.79599 | 5.23159 | 5.03545 | 7.43928 | 11.13903 | 9.21590 |
| | Minimum | | | 3.00 | 2.70 | 4.50 | 2.80 | 2.60 | 5.40 |
| | Maximum | | | 13.40 | 18.90 | 18.20 | 24.60 | 36.60 | 29.70 |
| | Percentiles | 25 | | 4.3000 | 5.2000 | 8.0000 | 10.6000 | 11.5000 | 9.7000 |
| | | 50 | | 7.2000 | 8.2000 | 11.0000 | 11.9000 | 12.5000 | 15.3000 |
| | | 75 | | 12.1000 | 10.8000 | 17.2000 | 20.6000 | 25.6000 | 27.1000 |
| B | N | Valid | | 7 | 7 | 7 | 7 | 7 | 7 |
| | | Lost | | 0 | 0 | 0 | 0 | 0 | 0 |
| | Mean | | | 4.8286 | 4.6714 | 5.6143 | 5.5714 | 7.4143 | 8.2571 |
| | Median | | | 3.9000 | 5.2000 | 4.9000 | 5.4000 | 5.8000 | 7.7000 |
| | SD | | | 2.78132 | 1.12207 | 2.59257 | 2.36130 | 3.56718 | 5.01825 |
| | Minimum | | | 3.30 | 2.60 | 3.10 | 2.20 | 4.30 | 2.00 |
| | Maximum | | | 11.10 | 5.70 | 10.30 | 9.40 | 14.10 | 17.90 |
| | Percentiles | 25 | | 3.5000 | 3.9000 | 3.8000 | 4.3000 | 4.6000 | 4.5000 |
| | | 50 | | 3.9000 | 5.2000 | 4.9000 | 5.4000 | 5.8000 | 7.7000 |
| | | 75 | | 4.1000 | 5.6000 | 8.0000 | 7.6000 | 9.9000 | 10.1000 |

The neutrophil level observed at different times for group A (p=0.070):

| | Group | | neutrophils (%) T0 | neutrophils (%) T1 | neutrophils (%) T2 | neutrophils (%) T3 | neutrophils (%) T4 | neutrophils (%) T5 |
|---|---|---|---|---|---|---|---|---|
| A | N | Valid | 7 | 7 | 7 | 7 | 7 | 7 |
| | | Lost | 0 | 0 | 0 | 0 | 0 | 0 |
| | Mean | | 87.1143 | 86.3143 | 81.2143 | 79.0714 | 77.8143 | 76.7286 |
| | Median | | 88.6000 | 86.9000 | 81.1000 | 75.8000 | 79.5000 | 79.7000 |
| | SD | | 6.82799 | 8.33175 | 6.01953 | 8.00411 | 12.25988 | 12.21757 |
| | Minimum | | 74.00 | 73.30 | 72.90 | 71.30 | 56.80 | 61.90 |
| | Maximum | | 95.20 | 95.40 | 91.80 | 92.90 | 94.10 | 91.90 |
| | Percentiles | 25 | 83.1000 | 78.7000 | 77.5000 | 74.1000 | 67.3000 | 65.7000 |
| | | 50 | 88.6000 | 86.9000 | 81.1000 | 75.8000 | 79.5000 | 79.7000 |
| | | 75 | 91.0000 | 94.8000 | 84.5000 | 87.6000 | 85.0000 | 89.6000 |
| B | N | Valid | 7 | 7 | 7 | 7 | 7 | 7 |
| | | Lost | 0 | 0 | 0 | 0 | 0 | 0 |
| | Mean | | 92.4286 | 92.2714 | 90.6429 | 91.7571 | 87.7857 | 87.9571 |
| | Median | | 94.3000 | 92.5000 | 92.2000 | 92.4000 | 88.4000 | 89.9000 |
| | SD | | 5.35435 | 2.84413 | 4.01325 | 3.77618 | 6.93023 | 6.84930 |
| | Minimum | | 80.50 | 87.30 | 83.80 | 84.90 | 77.30 | 76.30 |
| | Maximum | | 96.20 | 96.10 | 95.60 | 96.10 | 94.50 | 97.30 |
| | Percentiles | 25 | 92.9000 | 90.4000 | 87.0000 | 89.5000 | 80.5000 | 81.7000 |
| | | 50 | 94.3000 | 92.5000 | 92.2000 | 92.4000 | 88.4000 | 89.9000 |
| | | 75 | 94.9000 | 94.1000 | 93.3000 | 95.3000 | 94.2000 | 90.8000 |

The GOT level observed at different times for groups A (p=0.013) and B (p=0.077):

| | Group | | GOT T0 | GOT T1 | GOT T2 | GOT T3 | GOT T4 | GOT T5 |
|---|---|---|---|---|---|---|---|---|
| A | N | Valid | 7 | 7 | 7 | 6 | 7 | 7 |
| | | Lost | 0 | 0 | 0 | 1 | 0 | 0 |
| | Mean | | 60.4286 | 54.0000 | 41.7143 | 38.3333 | 36.2857 | 42.0000 |
| | Median | | 36.0000 | 40.0000 | 32.0000 | 22.5000 | 22.0000 | 25.0000 |
| | SD | | 48.56905 | 44.59821 | 37.72141 | 34.93232 | 33.16984 | 45.06292 |
| | Minimum | | 16.00 | 13.00 | 8.00 | 15.00 | 18.00 | 21.00 |
| | Maximum | | 147.00 | 145.00 | 122.00 | 106.00 | 110.00 | 144.00 |
| | Percentiles | 25 | 29.0000 | 26.0000 | 18.0000 | 17.2500 | 20.0000 | 23.0000 |
| | | 50 | 36.0000 | 40.0000 | 32.0000 | 22.5000 | 22.0000 | 25.0000 |
| | | 75 | 108.0000 | 74.0000 | 46.0000 | 61.0000 | 38.0000 | 30.0000 |
| B | N | Valid | 6 | 6 | 7 | 7 | 7 | 7 |
| | | Lost | 1 | 1 | 0 | 0 | 0 | 0 |
| | Mean | | 27.9500 | 38.8333 | 43.4286 | 33.8857 | 38.2286 | 33.2143 |
| | Median | | 19.2500 | 28.5000 | 25.0000 | 23.0000 | 23.0000 | 24.5000 |
| | SD | | 25.27795 | 22.24785 | 49.35199 | 22.87702 | 31.14534 | 27.45277 |
| | Minimum | | 11.00 | 20.00 | 13.00 | 15.00 | 13.00 | 15.00 |
| | Maximum | | 78.00 | 74.00 | 151.00 | 72.20 | 99.60 | 94.00 |
| | Percentiles | 25 | 11.9000 | 22.2500 | 16.0000 | 19.0000 | 18.0000 | 19.0000 |
| | | 50 | 19.2500 | 28.5000 | 25.0000 | 23.0000 | 23.0000 | 24.5000 |
| | | 75 | 40.5000 | 62.7500 | 53.0000 | 61.0000 | 60.0000 | 34.0000 |

The GPT level observed at different times for group B (p=0.004):

| | Group | | GPT T0 | GPT T1 | GPT T2 | GPT T3 | GPT T4 | GPT T5 |
|---|---|---|---|---|---|---|---|---|
| A | N | Valid | 7 | 7 | 7 | 7 | 7 | 7 |
| | | Lost | 0 | 0 | 0 | 0 | 0 | 0 |
| | Mean | | 51.0000 | 45.0000 | 40.2857 | 32.7143 | 30.5714 | 30.2857 |
| | Median | | 36.0000 | 32.0000 | 27.0000 | 31.0000 | 31.0000 | 27.0000 |
| | SD | | 54.22791 | 46.54747 | 29.78654 | 21.06114 | 19.26012 | 21.47645 |
| | Minimum | | 7.00 | 7.00 | 8.00 | 5.00 | 9.00 | 10.00 |
| | Maximum | | 167.00 | 143.00 | 79.00 | 56.00 | 59.00 | 73.00 |
| | Percentiles | 25 | 15.0000 | 16.0000 | 15.0000 | 15.0000 | 12.0000 | 13.0000 |
| | | 50 | 36.0000 | 32.0000 | 27.0000 | 31.0000 | 31.0000 | 27.0000 |
| | | 75 | 60.0000 | 55.0000 | 76.0000 | 54.0000 | 49.0000 | 40.0000 |
| B | N | Valid | 6 | 6 | 7 | 7 | 7 | 7 |
| | | Lost | 1 | 1 | 0 | 0 | 0 | 0 |
| | Mean | | 15.7167 | 25.5000 | 22.2857 | 16.2143 | 16.2286 | 12.2857 |
| | Median | | 14.0000 | 19.5000 | 20.0000 | 15.0000 | 17.0000 | 12.0000 |
| | SD | | 9.56147 | 18.09696 | 12.44607 | 7.78812 | 7.95188 | 7.04070 |
| | Minimum | | 5.50 | 12.00 | 11.00 | 7.00 | 8.00 | 4.00 |

-continued

| Group | | GPT T0 | GPT T1 | GPT T2 | GPT T3 | GPT T4 | GPT T5 |
|---|---|---|---|---|---|---|---|
| Maximum | | 33.50 | 60.00 | 43.00 | 28.00 | 31.00 | 23.00 |
| Percentiles | 25 | 9.6250 | 12.7500 | 12.0000 | 10.0000 | 9.0000 | 4.0000 |
| | 50 | 14.0000 | 19.5000 | 20.0000 | 15.0000 | 17.0000 | 12.0000 |
| | 75 | 20.6000 | 36.7500 | 36.0000 | 22.0000 | 19.0000 | 18.0000 |

The GGT level observed at different times for group A ($p=0.079$):

| Group | | | GGT T0 | GGT T1 | GGT T2 | GGT T3 | GGT T4 | GGT T5 |
|---|---|---|---|---|---|---|---|---|
| A | N | Valid | 7 | 7 | 7 | 7 | 7 | 7 |
| | | Lost | 0 | 0 | 0 | 0 | 0 | 0 |
| | Mean | | 150.2857 | 131.7143 | 130.2857 | 142.4286 | 147.7143 | 240.8571 |
| | Median | | 68.0000 | 56.0000 | 69.0000 | 74.0000 | 98.0000 | 163.0000 |
| | SD | | 158.16206 | 144.03786 | 140.32904 | 160.26526 | 134.40575 | 204.12858 |
| | Minimum | | 33.00 | 28.00 | 29.00 | 33.00 | 34.00 | 39.00 |
| | Maximum | | 418.00 | 377.00 | 398.00 | 481.00 | 432.00 | 610.00 |
| | Percentiles | 25 | 37.0000 | 30.0000 | 34.0000 | 46.0000 | 76.0000 | 112.0000 |
| | | 50 | 68.0000 | 56.0000 | 69.0000 | 74.0000 | 98.0000 | 163.0000 |
| | | 75 | 335.0000 | 296.0000 | 246.0000 | 210.0000 | 190.0000 | 436.0000 |
| B | N | Valid | 6 | 6 | 7 | 7 | 7 | 7 |
| | | Lost | 1 | 1 | 0 | 0 | 0 | 0 |
| | Mean | | 94.9333 | 94.6667 | 81.7143 | 119.1429 | 190.0000 | 176.5714 |
| | Median | | 108.0000 | 79.0000 | 83.0000 | 87.0000 | 110.0000 | 120.0000 |
| | SD | | 50.15283 | 53.64202 | 32.55618 | 89.37455 | 179.62090 | 183.81227 |
| | Minimum | | 31.60 | 32.00 | 39.00 | 40.00 | 37.00 | 37.00 |
| | Maximum | | 144.00 | 191.00 | 140.00 | 281.00 | 476.00 | 554.00 |
| | Percentiles | 25 | 35.6500 | 64.2500 | 51.0000 | 41.0000 | 40.0000 | 54.0000 |
| | | 50 | 108.0000 | 79.0000 | 83.0000 | 87.0000 | 110.0000 | 120.0000 |
| | | 75 | 141.7500 | 131.7500 | 94.0000 | 193.0000 | 396.0000 | 271.0000 |

If direct differences between groups A and B are compared at each moment in time independently (Mann-Whitney test for independent samples), at moment T2, there are differences between A and B in red blood cell ($p=0.026$), hemoglobin ($p=0.038$) and hematocrit ($p=0.053$) levels.

In lymphocyte levels, there are differences at all times:

| | lymphocytes 10_3 ml T0 | lymphocytes (%) T1 | lymphocytes (%) T2 | lymphocytes (%) T3 | lymphocytes (%) T4 | lymphocytes (%) T5 |
|---|---|---|---|---|---|---|
| Mann-Whitney U | 11.000 | 9.500 | 6.500 | 6.000 | 10.000 | 9.000 |
| Wilcoxon W | 39.000 | 37.500 | 34.500 | 34.000 | 38.000 | 37.000 |
| Z | −1.727 | −1.919 | −2.302 | −2.366 | −1.853 | −1.981 |
| Asymp. sig. (2 – tailed) | 0.084 | 0.055 | 0.021 | 0.018 | 0.064 | 0.048 |
| Exact sig. [2 * (1 – tailed sig.)] | 0.097a | 0.053a | 0.017a | 0.017a | 0.073a | 0.053a |

There are differences in neutrophil levels between A and B at T2 ($p=0.007$) and T3 ($p=0.011$)

There are differences in GPT levels between A and B at T5 ($p=0.038$)

There are no significant differences in urea levels over time; they remain virtually identical in both groups (Friedman test, $p=0.205$ for group A and $p=0.959$ for group B):

UREA

| Group | | | urea T0 | urea T1 | urea T2 | urea T3 | urea T4 | urea T5 |
|---|---|---|---|---|---|---|---|---|
| A | N | Valid | 7 | 7 | 7 | 7 | 7 | 7 |
| | | Lost | 0 | 0 | 0 | 0 | 0 | 0 |

-continued

| Group | | | urea T0 | urea T1 | urea T2 | urea T3 | urea T4 | urea T5 |
|---|---|---|---|---|---|---|---|---|
| | Mean | | 51.4286 | 47.7143 | 45.0000 | 39.4286 | 40.2857 | 43.5714 |
| | Median | | 57.0000 | 61.0000 | 60.0000 | 57.0000 | 54.0000 | 55.0000 |
| | SD | | 26.13973 | 27.13985 | 28.56571 | 25.81897 | 30.05946 | 31.57455 |
| | Minimum | | 9.00 | 5.00 | 10.00 | 7.00 | 2.00 | 4.00 |
| | Maximum | | 83.00 | 74.00 | 77.00 | 67.00 | 72.00 | 79.00 |
| | Percentiles | 25 | 23.0000 | 19.0000 | 14.0000 | 11.0000 | 8.0000 | 10.0000 |
| | | 50 | 57.0000 | 61.0000 | 60.0000 | 57.0000 | 54.0000 | 55.0000 |
| | | 75 | 69.0000 | 73.0000 | 71.0000 | 58.0000 | 66.0000 | 78.0000 |
| B | N | Valid | 7 | 7 | 7 | 7 | 7 | 7 |
| | | Lost | 0 | 0 | 0 | 0 | 0 | 0 |
| | Mean | | 111.2857 | 115.0000 | 109.0000 | 114.2857 | 117.5714 | 115.7143 |
| | Median | | 117.0000 | 120.0000 | 92.0000 | 100.0000 | 90.0000 | 99.0000 |
| | SD | | 37.94168 | 33.78856 | 46.38965 | 54.75921 | 73.16160 | 85.85397 |
| | Minimum | | 62.00 | 68.00 | 66.00 | 69.00 | 44.00 | 30.00 |
| | Maximum | | 169.00 | 172.00 | 191.00 | 213.00 | 250.00 | 260.00 |
| | Percentiles | 25 | 64.0000 | 84.0000 | 71.0000 | 71.0000 | 61.0000 | 55.0000 |
| | | 50 | 117.0000 | 120.0000 | 92.0000 | 100.0000 | 90.0000 | 99.0000 |
| | | 75 | 133.0000 | 130.0000 | 150.0000 | 166.0000 | 182.0000 | 208.0000 |

However, if urea levels between the two groups are compared at each measured moment in time, urea levels are higher in group B at all the measured moments except the last one. The differences are statistically significant:

| | Group | N | Mean | SD | SEM | p |
|---|---|---|---|---|---|---|
| urea T0 | A | 7 | 51.4286 | 26.13973 | 9.87989 | 0.011 |
| | B | 7 | 111.2857 | 37.94168 | 14.34061 | |
| urea T1 | A | 7 | 47.7143 | 27.13985 | 10.25790 | 0.002 |
| | B | 7 | 115.0000 | 33.78856 | 12.77087 | |
| urea T2 | A | 7 | 45.0000 | 28.56571 | 10.79682 | 0.004 |
| | B | 7 | 109.0000 | 46.38965 | 17.53364 | |
| urea T3 | A | 7 | 39.4286 | 25.81897 | 9.75865 | 0.001 |
| | B | 7 | 114.2857 | 54.75921 | 20.69704 | |

-continued

| | Group | N | Mean | SD | SEM | p |
|---|---|---|---|---|---|---|
| urea T4 | A | 7 | 40.2857 | 30.05946 | 11.36141 | 0.026 |
| | B | 7 | 117.5714 | 73.16160 | 27.65248 | |
| urea T5 | A | 7 | 43.5714 | 31.57455 | 11.93406 | 0.073 |
| | B | 7 | 115.7143 | 85.85397 | 32.44975 | |

In addition, the progression over time of the following parameters in each group separately has not shown significant differences:

CREATININE

There are no significant differences in creatinine levels over time; they remain identical in both groups (Friedman test, p=0.122 for group A and p=0.831 for group B):

| Group | | | creatinine T0 | creatinine T1 | creatinine T2 | creatinine T3 | creatinine T4 | creatinine T5 |
|---|---|---|---|---|---|---|---|---|
| A | N | Valid | 7 | 7 | 7 | 7 | 7 | 7 |
| | | Lost | 0 | 0 | 0 | 0 | 0 | 0 |
| | Mean | | 1.7614 | 1.4957 | 1.3343 | 1.1929 | 1.1300 | 1.0571 |
| | Median | | 1.4400 | 1.1000 | .9700 | 1.1200 | 1.2200 | 0.7600 |
| | SD | | 1.15338 | 0.99052 | 0.90526 | 0.79229 | 0.61709 | 0.61302 |
| | Minimum | | 0.49 | 0.48 | 0.46 | 0.39 | 0.46 | 0.40 |
| | Maximum | | 3.70 | 2.80 | 2.47 | 2.18 | 2.05 | 1.94 |
| | Percentiles | 25 | 0.7500 | 0.6800 | 0.5000 | 0.4100 | 0.5200 | 0.5900 |
| | | 50 | 1.4400 | 1.1000 | 0.9700 | 1.1200 | 1.2200 | 0.7600 |
| | | 75 | 2.9100 | 2.7400 | 2.2200 | 1.9500 | 1.6700 | 1.7100 |
| B | N | Valid | 7 | 7 | 7 | 7 | 7 | 7 |
| | | Lost | 0 | 0 | 0 | 0 | 0 | 0 |
| | Mean | | 2.1157 | 2.1000 | 1.8843 | 1.8357 | 1.7600 | 1.5829 |
| | Median | | 2.0400 | 1.9700 | 1.9600 | 1.4100 | 1.6900 | 1.7200 |
| | SD | | 1.11884 | 0.84766 | 0.79521 | 0.93259 | 0.99698 | 1.05880 |
| | Minimum | | 0.54 | 0.80 | 0.64 | 0.67 | 0.54 | 0.39 |
| | Maximum | | 4.18 | 3.47 | 2.85 | 3.10 | 2.77 | 2.89 |
| | Percentiles | 25 | 1.6000 | 1.5800 | 1.1900 | 1.2300 | 00.7600 | 0.6100 |
| | | 50 | 2.0400 | 1.9700 | 1.9600 | 1.4100 | 1.6900 | 1.7200 |
| | | 75 | 2.6300 | 2.7000 | 2.7400 | 2.8900 | 2.7600 | 2.8200 |

If creatinine levels between the two groups are compared at each measured moment in time, it can be seen that there are no statistically significant differences in creatinine levels between groups A and B:

|  | Group | N | Mean | SD | SEM | p |
|---|---|---|---|---|---|---|
| creatinine T0 | A | 7 | 1.7614 | 1.15338 | 0.43594 | 0.456 |
|  | B | 7 | 2.1157 | 1.11884 | 0.42288 |  |
| creatinine T1 | A | 7 | 1.4957 | 0.99052 | 0.37438 | 0.318 |
|  | B | 7 | 2.1000 | 0.84766 | 0.32039 |  |
| creatinine T2 | A | 7 | 1.3343 | 0.90526 | 0.34216 | 0.318 |
|  | B | 7 | 1.8843 | 0.79521 | 0.30056 |  |
| creatinine T3 | A | 7 | 1.1929 | 0.79229 | 0.29946 | 0.165 |
|  | B | 7 | 1.8357 | 0.93259 | 0.35249 |  |
| creatinine T4 | A | 7 | 1.1300 | 0.61709 | 0.23324 | 0.209 |
|  | B | 7 | 1.7600 | 0.99698 | 0.37682 |  |
| creatinine T5 | A | 7 | 1.0571 | 0.61302 | 0.23170 | 0.318 |
|  | B | 7 | 1.5829 | 1.05880 | 0.40019 |  |

LDH

There are no significant differences in LDH levels over time; they remain virtually identical in both groups (Friedman test, p=0.355 for group A and p=0.921 for group B):

| Group |  |  | LDH T0 | LDH T1 | LDH T2 | LDH T3 | LDH T4 | LDH T5 |
|---|---|---|---|---|---|---|---|---|
| A | N | Valid | 7 | 7 | 7 | 7 | 7 | 7 |
|  |  | Lost | 0 | 0 | 0 | 0 | 0 | 0 |
|  | Mean |  | 708.5714 | 685.8571 | 638.0000 | 658.7143 | 602.4286 | 707.8571 |
|  | Median |  | 561.0000 | 631.0000 | 418.0000 | 499.0000 | 380.0000 | 552.0000 |
|  | SD |  | 345.48992 | 345.16538 | 474.81435 | 445.02723 | 458.08255 | 354.42462 |
|  | Minimum |  | 504.00 | 320.00 | 327.00 | 377.00 | 364.00 | 397.00 |
|  | Maximum |  | 1474.00 | 1369.00 | 1677.00 | 1659.00 | 1623.00 | 1421.00 |
|  | Percentiles | 25 | 524.0000 | 421.0000 | 405.0000 | 480.0000 | 367.0000 | 491.0000 |
|  |  | 50 | 561.0000 | 631.0000 | 418.0000 | 499.0000 | 380.0000 | 552.0000 |
|  |  | 75 | 713.0000 | 836.0000 | 714.0000 | 570.0000 | 556.0000 | 912.0000 |
| B | N | Valid | 6 | 7 | 7 | 7 | 7 | 7 |
|  |  | Lost | 1 | 0 | 0 | 0 | 0 | 0 |
|  | Mean |  | 430.6667 | 591.4286 | 580.2857 | 570.5714 | 544.4286 | 609.5714 |
|  | Median |  | 420.0000 | 565.0000 | 545.0000 | 532.0000 | 590.0000 | 537.0000 |
|  | SD |  | 156.18024 | 142.31989 | 189.49557 | 159.89982 | 187.55964 | 257.69805 |
|  | Minimum |  | 197.00 | 359.00 | 391.00 | 329.00 | 305.00 | 351.00 |
|  | Maximum |  | 617.00 | 781.00 | 979.00 | 811.00 | 789.00 | 1066.00 |
|  | Percentiles | 25 | 306.5000 | 540.0000 | 468.0000 | 465.0000 | 343.0000 | 408.0000 |
|  |  | 50 | 420.0000 | 565.0000 | 545.0000 | 532.0000 | 590.0000 | 537.0000 |
|  |  | 75 | 594.5000 | 756.0000 | 611.0000 | 697.0000 | 683.0000 | 819.0000 |

If LDH levels between the two groups are compared at each measured moment in time, LDH levels are higher in group A at all the measured times, although the differences are not statistically significant:

|  | Group | N | Mean | SD | SEM | p |
|---|---|---|---|---|---|---|
| LDH T0 | A | 7 | 708.5714 | 345.48992 | 130.58292 | 0.073 |
|  | B | 6 | 430.6667 | 156.18024 | 63.76032 |  |
| LDH T1 | A | 7 | 685.8571 | 345.16538 | 130.46025 | 0.805 |
|  | B | 7 | 591.4286 | 142.31989 | 53.79186 |  |
| LDH T2 | A | 7 | 638.0000 | 474.81435 | 179.46296 | 0.535 |
|  | B | 7 | 580.2857 | 189.49557 | 71.62259 |  |
| LDH T3 | A | 7 | 658.7143 | 445.02723 | 168.20448 | 0.710 |
|  | B | 7 | 570.5714 | 159.89982 | 60.43645 |  |
| LDH T4 | A | 7 | 602.4286 | 458.08255 | 173.13893 | 0.710 |
|  | B | 7 | 544.4286 | 187.55964 | 70.89088 |  |
| LDH T5 | A | 7 | 707.8571 | 354.42462 | 133.95991 | 0.620 |
|  | B | 7 | 609.5714 | 257.69805 | 97.40071 |  |

The invention claimed is:

1. A pharmaceutically acceptable composition comprising propylene glycol, polyethylene glycol and melatonin or a, salt, thereof;
   wherein the melatonin is present in the composition at a concentration of between 0.1 and 30 grams per every 100 ml of the total solution (w/v);
   wherein the composition is in the form of a pharmaceutically acceptable injectable solution further comprising water or a saline solution; wherein the composition does not comprise ethanol; and
   wherein the composition is stable for more than 3 months at 25° C.

2. The composition according to claim 1, wherein the proportion of propylene glycol in the composition is between 5 and 50 grams per every 100 ml of the total solution (w/v).

3. The composition according to claim 2, wherein the proportion of polyethylene glycol in the composition is between 5 and 50 grams per every 100 ml of the total solution (w/v).

4. The composition according to claim 3, comprising additional pharmaceutically acceptable excipients.

5. The composition according to claim 1, comprising a second active ingredient.

6. The composition according to claim 1 in the form of intravenous injectable.

7. A method of treating sepsis in a subject in need thereof, the method comprising administering to said subject a composition of claim 1.

8. A method for preparing the pharmaceutically acceptable injectable composition of claim 1, comprising mixing water, propylene glycol, polyethylene glycol and melatonin or a, salt, thereof.

9. The method according to claim 7, wherein the composition is administered by perfusion.

10. The method according to claim 7, wherein the composition is administered over time between 1 and 30 days.

11. The composition according to claim 1, wherein the composition is stable for at least 6 months at 25° C.

* * * * *

UNITED STATES PATENT AND TRADEMARK OFFICE
CERTIFICATE OF CORRECTION

| | |
|---|---|
| PATENT NO. | : 11,344,531 B2 |
| APPLICATION NO. | : 15/129327 |
| DATED | : May 31, 2022 |
| INVENTOR(S) | : Dario Acuña Castroviejo et al. |

Page 1 of 1

It is certified that error appears in the above-identified patent and that said Letters Patent is hereby corrected as shown below:

On the Title Page

Item '(72) Inventors' Line 11, please replace "Carmen Olmedo Martin, Granada (ES);" with
-- Carmen Olmedo Martin, Sevilla (ES); --

In the Claims

At Column 32, Claim number 1, Lines 2-4, please replace "A pharmaceutically acceptable composition comprising propylene glycol, polyethylene glycol and melatonin or a, salt, thereof;" with
-- A pharmaceutically acceptable composition comprising propylene glycol, polyethylene glycol and melatonin or a salt thereof; --

At Column 32, Claim number 8, Lines 56-59, replace "A method for preparing the pharmaceutically acceptable injectable composition of claim 1, comprising mixing water, propylene glycol, polyethylene glycol and melatonin or a, salt, thereof." with -- A method for preparing the pharmaceutically acceptable injectable composition of claim 1, comprising mixing water, propylene glycol, polyethylene glycol and melatonin or a salt thereof. --

Signed and Sealed this
Sixteenth Day of August, 2022

Katherine Kelly Vidal
*Director of the United States Patent and Trademark Office*